(12) United States Patent
Brown

(10) Patent No.: US 9,966,668 B1
(45) Date of Patent: May 8, 2018

(54) SEMICONDUCTOR ANTENNA

(71) Applicant: Robert G. Brown, Tustin, CA (US)

(72) Inventor: Robert G. Brown, Tustin, CA (US)

(73) Assignee: ROCKWELL COLLINS, INC., Cedar Rapids, IA (US)

( * ) Notice: Subject to any disclaimer, the term of this patent is extended or adjusted under 35 U.S.C. 154(b) by 196 days.

(21) Appl. No.: 14/278,547

(22) Filed: May 15, 2014

(51) Int. Cl.
*H01Q 21/00* (2006.01)
*H01Q 23/00* (2006.01)

(52) U.S. Cl.
CPC ............ *H01Q 21/00* (2013.01); *H01Q 23/00* (2013.01)

(58) Field of Classification Search
CPC ....... H01Q 1/2283; H01Q 21/061; H01Q 3/26
USPC .......................... 343/893, 745, 824, 656, 458
See application file for complete search history.

(56) References Cited

U.S. PATENT DOCUMENTS

| | | | |
|---|---|---|---|
| 8,492,727 B1 | 7/2013 | Brown et al. | |
| 2010/0156573 A1* | 6/2010 | Smith | H01P 3/081 333/239 |
| 2010/0258919 A1* | 10/2010 | Makarov | H01Q 1/2283 257/656 |
| 2011/0163296 A1* | 7/2011 | Pace | B82Y 15/00 257/24 |
| 2011/0170103 A1 | 7/2011 | Gomez Rivas et al. | |
| 2012/0074323 A1 | 3/2012 | Gomez Rivas et al. | |
| 2013/0248936 A1* | 9/2013 | Alexopoulos | H01Q 1/2283 257/204 |
| 2013/0293436 A1* | 11/2013 | Blech | H01P 1/182 343/835 |

OTHER PUBLICATIONS

Giannini et al, Scattering efficiency and near field enhancement of active semiconductor plasmonic antennas at terahertz frequencies, Optics Express, vol. 18, p. 2797 (2010).
Jain et al, Semiconductor Antenna: A New Device in Millimeter- and Submillimeter-Wave Integrated Circuits, IEEE Trans. Microwave Theory and Techniques, MTT-32, p. 204, (1984).
Milligan, Modern Antenna Design, McGraw-Hill, (1985) 633 pages.

* cited by examiner

*Primary Examiner* — Dameon E Levi
*Assistant Examiner* — Collin Dawkins
(74) *Attorney, Agent, or Firm* — Donna P. Suchy; Daniel M. Barbieri

(57) ABSTRACT

A semiconductor antenna includes an antenna region. The antenna region includes semiconductor nano-antennas. The semiconductor nano-antennas are formed of a semiconductor material have a doping concentration such that the real part of the permittivity of the semiconductor material is negative over at least a portion of radio frequencies from 1 MHz to 300 GHz.

14 Claims, 18 Drawing Sheets

US 9,966,668 B1

SEMICONDUCTOR ANTENNA

FIELD OF INVENTION

The present invention relates to semiconductor nano-antennas and devices incorporating such nano-antennas.

BACKGROUND

The principles and practice of antenna design and operation is well known, and summarized, for example, in [T. A. Milligan, Modern Antenna Design, McGraw-Hill (1985).]. Antenna designs include many forms. For example, antenna designs include simple dipole/gap antennas, log-periodic antennas, and Yagi antennas. Further, phased arrays of antenna elements are widely used in Radar for beam parameter control and steering. One of the simplest antennas is a dipole with a gap. Electric field strengths in a correctly designed gap can exceed $10^3$ to $10^4$ of the incident field strength.

In a typical antenna, usually some kind of gap antenna (or array of such antennas) is constructed from metal, whose characteristic size is on the order of half the radio frequency (RF) wavelength. At 100 GHz the wavelength is 3 mm, at 10 GHz it is 30 mm and at 1 GHz it is 300 mm (~1 foot), which RF requires an antenna with a characteristic size, which is physically large compared to many applications, such as for satellite applications. Such a large scale is required for the use of metal antennas.

Jain et al. discuss the possibility of a semiconductor antenna [F. C. Jain et al, 'Semiconductor Antenna: A New Device in Millimeter- and Submillimeter-Wave Integrated Circuits', IEEE Trans. Microwave Theory and Techniques, MTT-32, p. 204, (1984).], and briefly speculate on the concept of monolithic antenna to integrated circuit (IC) integration, perhaps on sapphire. Jain et al., however, do not mention plasmons, nor do they mention resonantly coupled arrays of semiconductor antennas for signal enhancement.

Semiconductor antennas comprising a doped semiconductor material have been demonstrated, for example, in U.S. Patent Application Publications 2011/0170103 and 2012/0074323 to Rivas et al. In particular, Rivas et al. disclose a semiconductor antenna made of doped InSb, and operated in the THz region. Such a semiconductor antenna operating in the THz region, however, is of little use to RF communication engineers as the signals in THz region are heavily absorbed in the atmosphere by water droplets. Instead such a THz region antenna is appropriate for use as a biosensor, as biological material changes affect local refractive index and thus affect antenna resonances. The antennas in Rivas et al are not mentioned as appropriate for use in communications purposes, nor is there any mention of sub THz operations.

SUMMARY

According to one embodiment, there is provided a semiconductor antenna comprising: an antenna region comprising semiconductor nano-antennas, wherein the semiconductor nano-antennas are formed of a semiconductor material have a doping concentration such that the real part of the permittivity of the semiconductor material is negative over at least a portion of radio frequencies from 1 MHz to 300 GHz.

According to one aspect of the embodiment, the semiconductor material is one of a single, binary, ternary or quarternary semiconductor compound.

According to another aspect of the embodiment, the semiconductor material is selected from the group consisting of silicon, germanium, and gallium arsenide.

According to another aspect of the embodiment, the semiconductor nano-antennas are in the shape of dipole gap, Yagi, or log-periodic antennas.

According to another aspect of the embodiment, the semiconductor nano-antennas are arranged in an array of resonantly coupled nano-antennas.

According to another aspect of the embodiment, the characteristic dimensions of semiconductor nano-antennas are in the range of nanometers to millimeters in spatial scale.

According to another aspect of the embodiment, the semiconductor nano-antennas are arranged in a square or rectangular array.

According to another aspect of the embodiment, the semiconductor nano-antennas are aligned with crystal plane or atom vector directions of the semiconductor material.

According to another aspect of the embodiment, an electronic device, comprises the semiconductor antenna; and one or more electronic components coupled to the semiconductor antenna, and arranged to receive an electrical signal from the semiconductor antenna.

According to another aspect of the embodiment, the one or more electronic components comprise components of a MOSFET.

According to another aspect of the embodiment, the one or more electronic components are monolithically integrated with the semiconductor antenna on the same chip.

According to another aspect of the embodiment, the one or more electronic components are monolithically integrated with the semiconductor antenna on the same chip.

According to another aspect of the embodiment, the gap of the semiconductor antenna is aligned with a gate region of the MOSFET.

According to another aspect of the embodiment, an electronic circuit comprises the electronic device.

According to another aspect of the embodiment, the electronic circuit is one of a radio receiver, radio transmitter, radar unit, avionics unit, satellite, chemical sensor, or biological sensor.

DETAILED DESCRIPTION

Permittivity for 1 GHz to 100 GHz Regime

The present inventor has contemplated the construction semiconductor nano-antennas for sub THz operation, i.e, GHz and lower frequencies. A key question addressed by the present inventor is whether or not plasmons can be created and supported in propagation at GHz and sub GHz frequencies. The semiconductor antennas described herein are based on semiconductor material having an appropriate doping to support the plasmon effect, in particular in the sub THz regime.

A fundamental condition for supporting a plasmon and its propagation is that $\epsilon'$ (real permittivity) of the material is negative, at frequencies below the plasma frequency.

Appropriate physics and math for calculating the permittivity in the THz regime is summarized in [V. Giannini et al, 'Scattering efficiency and near field enhancement of active semiconductor plasmonic antennas at terahertz frequencies', Optics Express, vol. 18, p. 2797 (2010).] As described, the permittivity function $\epsilon(\omega)$ of semiconductors at THz frequencies is well described by the Drude model for free carriers $\epsilon(\omega)=\epsilon(\infty)-\omega_p^2/(\omega^2+i\omega\gamma)$, where $\epsilon(\infty)$ is the high-frequency permittivity, $\gamma=1/\tau$ is the carrier momentum relaxation rate and $\tau$ is the average collision time of the charge carriers. The momentum relaxation rate $\gamma$ is related to the carrier mobility $\mu$ by $\gamma=m^*\mu/e$, where $m^*$ is the effective mass of the charge carriers and e the elementary charge. The plasma frequency $\omega_p$ is defined as $\omega_p^2=e^2N/(\epsilon_0 m^*)$, where N is the free carrier concentration and $\epsilon_0$ the vacuum permittivity.

In order to determine whether or not semiconductor antenna operation below the THz regime is possible, calculations are performed for different semiconductors to determine if $\epsilon'$ (real permittivity) of the material is negative, at frequencies in the regime of 1 GHz to 100 GHz. In particular, calculations are performed for the 1 GHz to 100 GHz regime, for different semiconductor materials under varying doping density conditions, to determine if any kind of plasmon can be created and supported in the 1 GHz to 100 GHz regime.

Figure 1A:
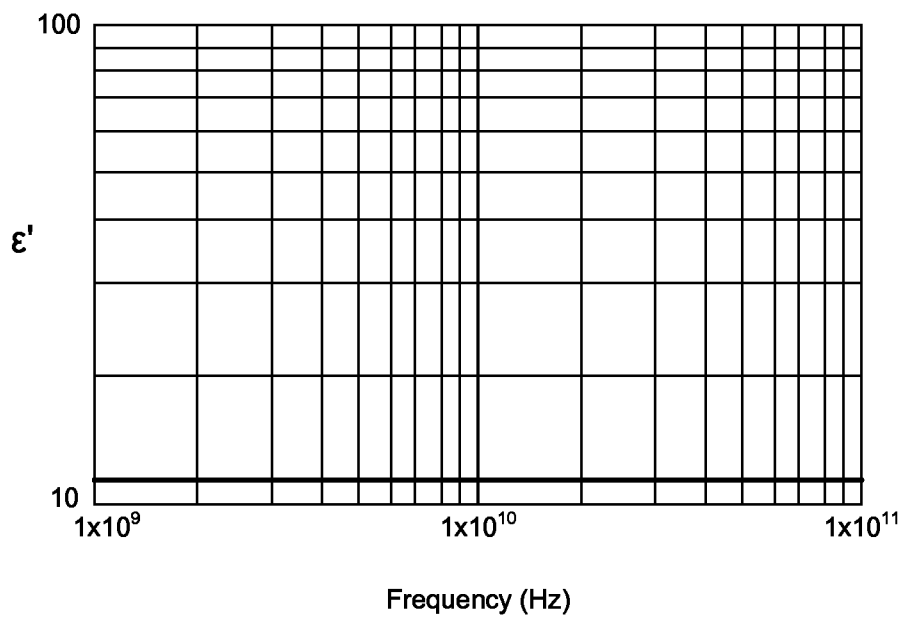
FIG. 1A is a graph illustrating the real permittivity of intrinsic silicon as a function of radiation frequency.
Figure 1B:
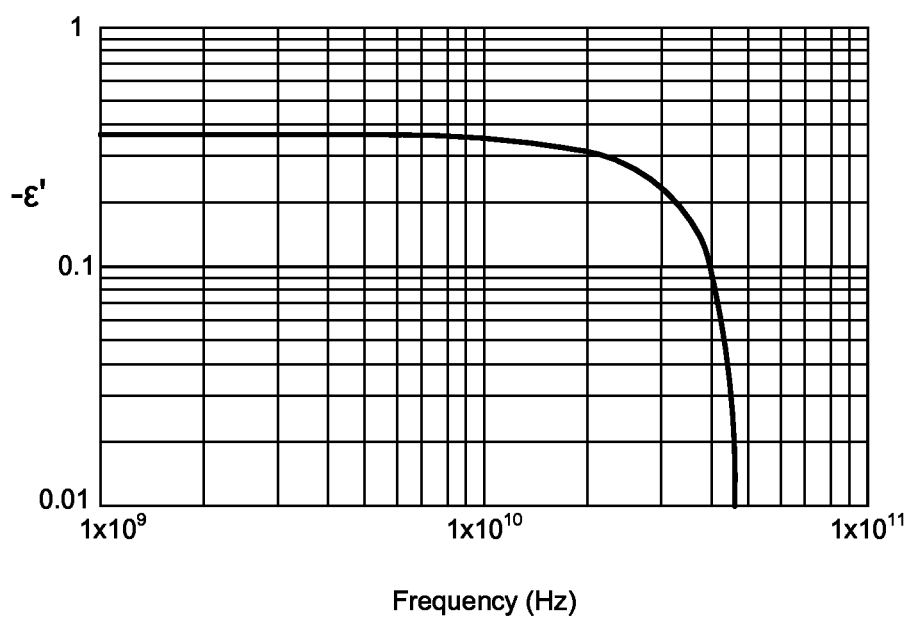
FIG. 1B is a graph illustrating the negative real permittivity of silicon doped to a carrier density of $10^{16}$ per cc as a function of radiation frequency.
Figure 1C:
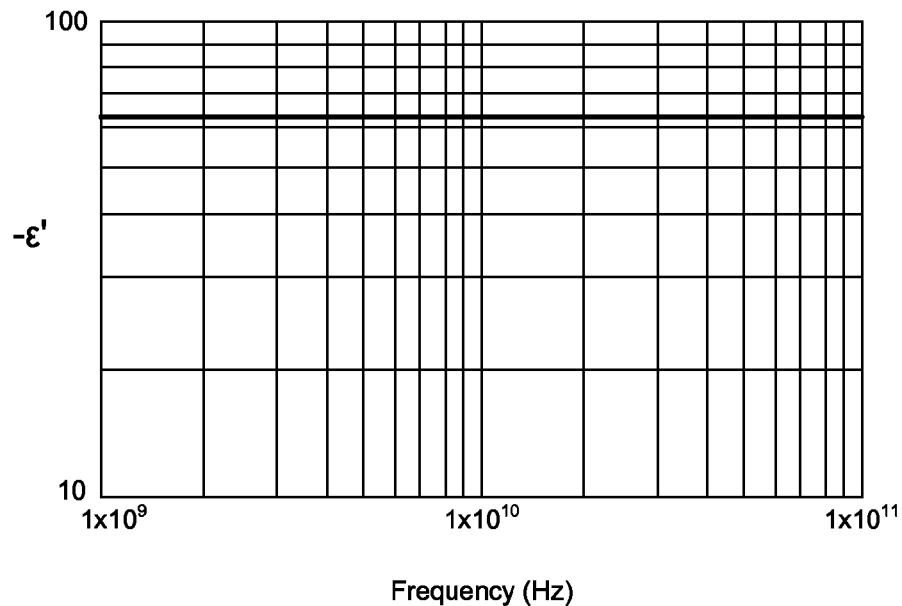
FIG. 1C is a graph illustrating the negative real permittivity of silicon doped to a carrier density of $10^{18}$ per cc as a function of radiation frequency.
Figure 1D:
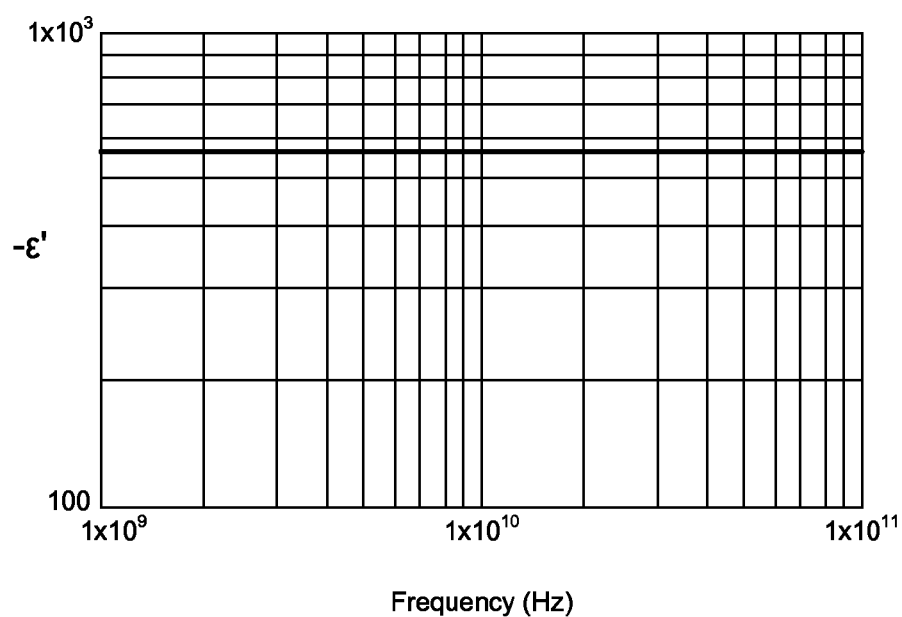
FIG. 1D is a graph illustrating the negative real permittivity of silicon doped to a carrier density of $10^{20}$ per cc as a function of radiation frequency.

The results of the real permittivity calculation for silicon as a function of frequency at various carrier doping densities for Si is shown in FIGS. 1A-1D. FIG. 1A illustrates no doping, that is intrinsic Si. The real permittivity, $\epsilon'$, over the entire range 1 GHz to 100 GHz is positive, and thus plasmons may not be supported. FIG. 1B illustrates $-\epsilon'$ as a function of frequency for a carrier density of $10^{16}$ per cc. As can be seen in FIG. 1B, $\epsilon'$ is negative up to about 47 GHz, thus supporting plasmons over a portion of the frequency range of 1 to 100 GHz. FIG. 1C illustrates $-\epsilon'$ as a function of frequency for a carrier density of $10^{18}$ per cc. As can be seen in FIG. 1C, $\epsilon'$ is negative over the entire range of 1 GHz to 100 GHz, thus supporting plasmons over the entire range. FIG. 1D illustrates $-\epsilon'$ as a function of frequency for a carrier density of $10^{20}$ per cc. As can be seen in FIG. 1D, $\epsilon'$ is negative over the entire range of 1 GHz to 100 GHz, thus supporting plasmons over the entire range.

Figure 2A:
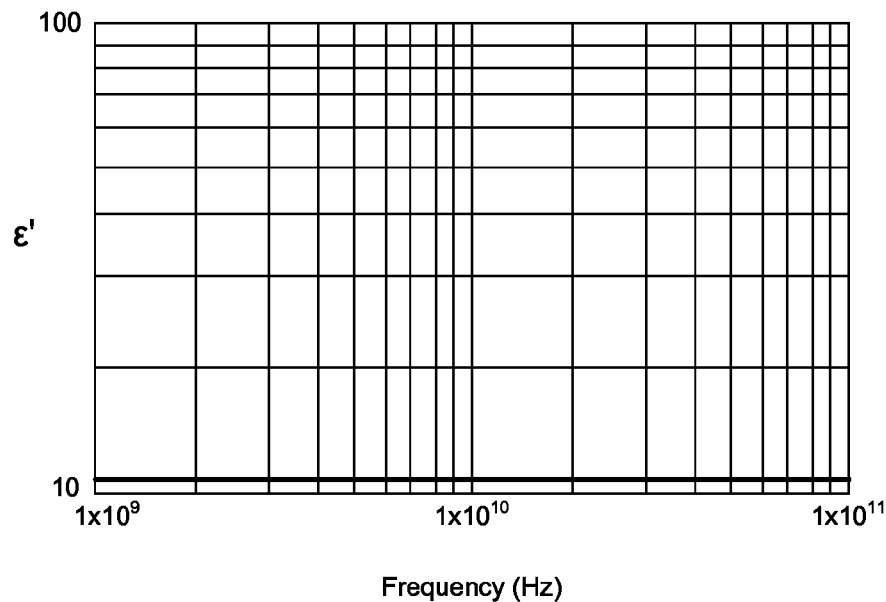
FIG. 2A is a graph illustrating the real permittivity of intrinsic GaAs as a function of radiation frequency.
Figure 2B:
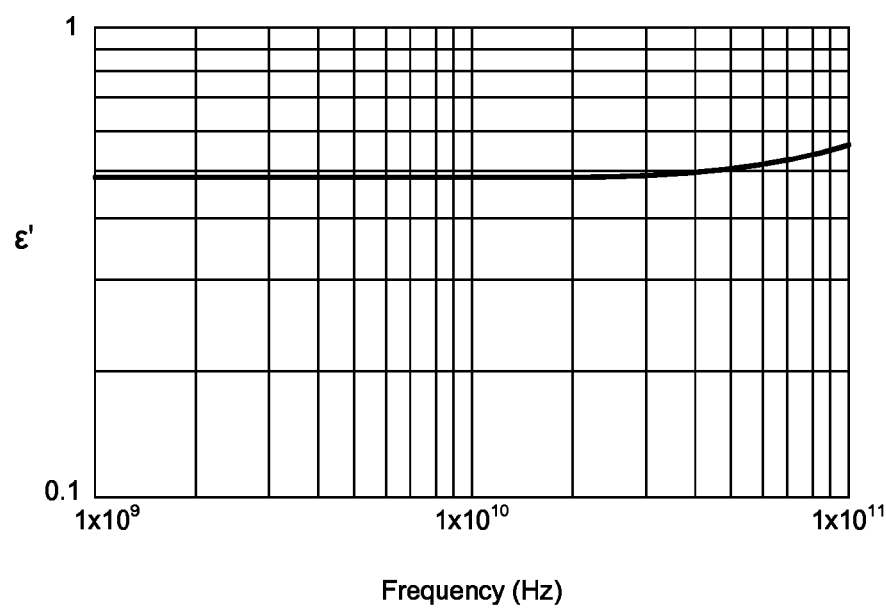
FIG. 2B is a graph illustrating the real permittivity of GaAs doped to a carrier density of $10^{16}$ per cc as a function of radiation frequency.
Figure 2C:
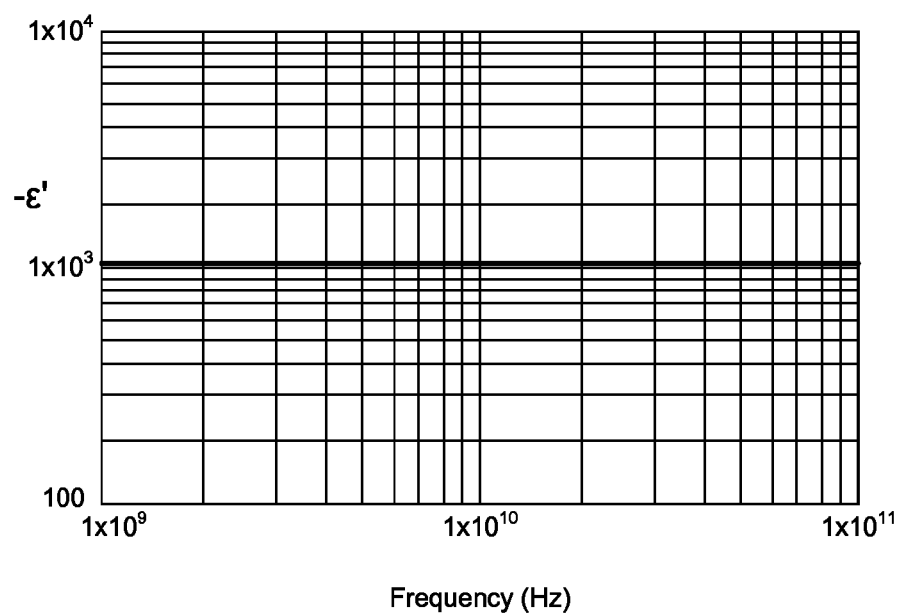
FIG. 2C is a graph illustrating the negative real permittivity of GaAs doped to a carrier density of $10^{18}$ per cc as a function of radiation frequency.
Figure 2D:
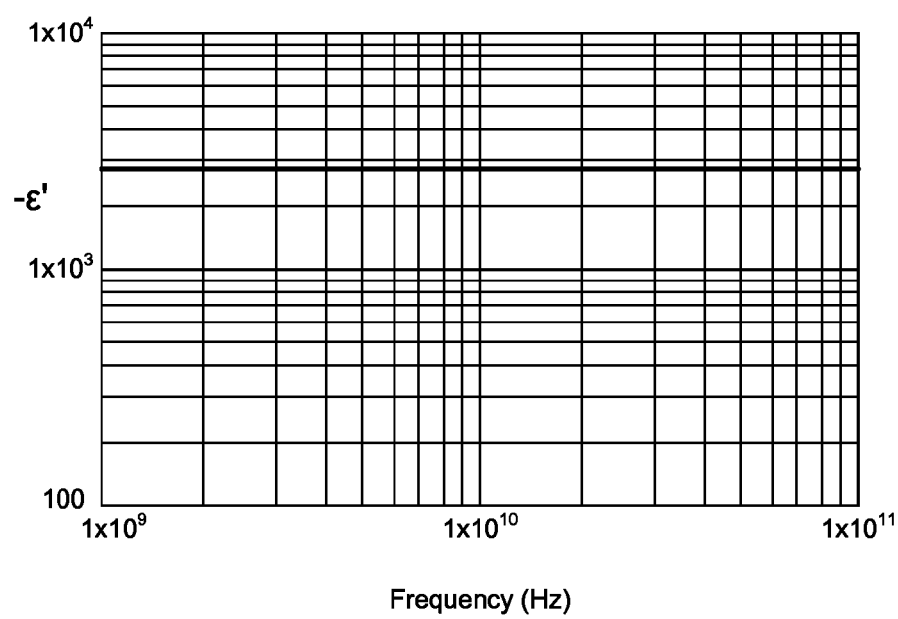
FIG. 2D is a graph illustrating the negative real permittivity of GaAs doped to a carrier density of $10^{20}$ per cc as a function of radiation frequency.

The results of the real permittivity calculation for GaAs as a function of frequency at various carrier doping densities is shown in FIGS. 2A-2D. FIG. 2A illustrates no doping, that is intrinsic GaAs. The real permittivity, $\epsilon'$, over the entire range 1 GHz to 100 GHz is positive, and thus plasmons may not be supported. FIG. 2B illustrates $\epsilon'$ as a function of frequency for a carrier density of $10^{18}$ per cc. Again the real permittivity, $\epsilon'$, over the entire range 1 GH to 100 GHz is positive, and thus plasmons may not be supported. FIG. 2C illustrates $-\epsilon'$ as a function of frequency for a carrier density of $10^{18}$ per cc. As can be seen in FIG. 2C, $\epsilon'$ is negative over the entire range of 1 GHz to 100 GHz, thus supporting plasmons over the entire range. FIG. 2D illustrates $-\epsilon'$ as a function of frequency for a carrier density of $10^{20}$ per cc. As can be seen in FIG. 2D, $\epsilon'$ is negative over the entire range of 1 GHz to 100 GHz, thus supporting plasmons over the entire range.

Figure 3A:
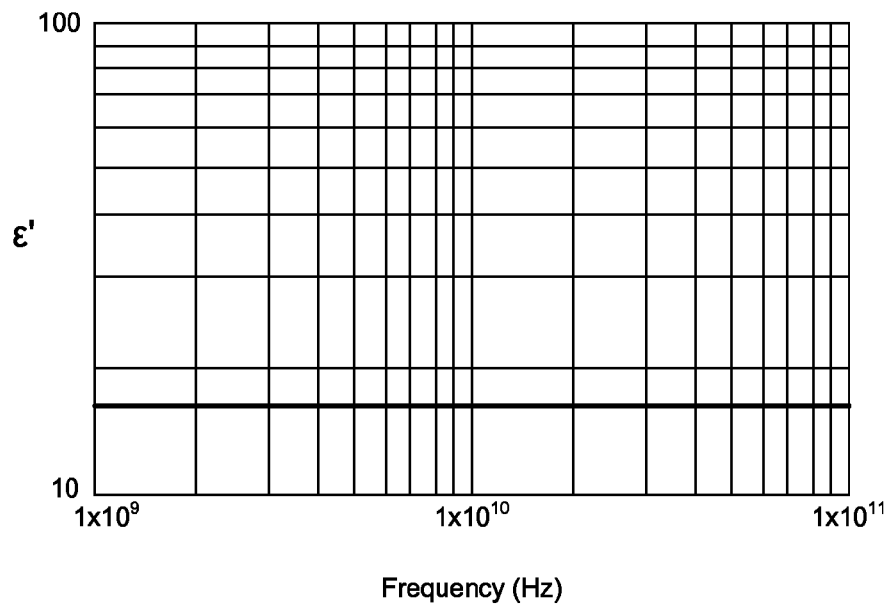
FIG. 3A is a graph illustrating the real permittivity of intrinsic Ge as a function of radiation frequency.
Figure 3B:
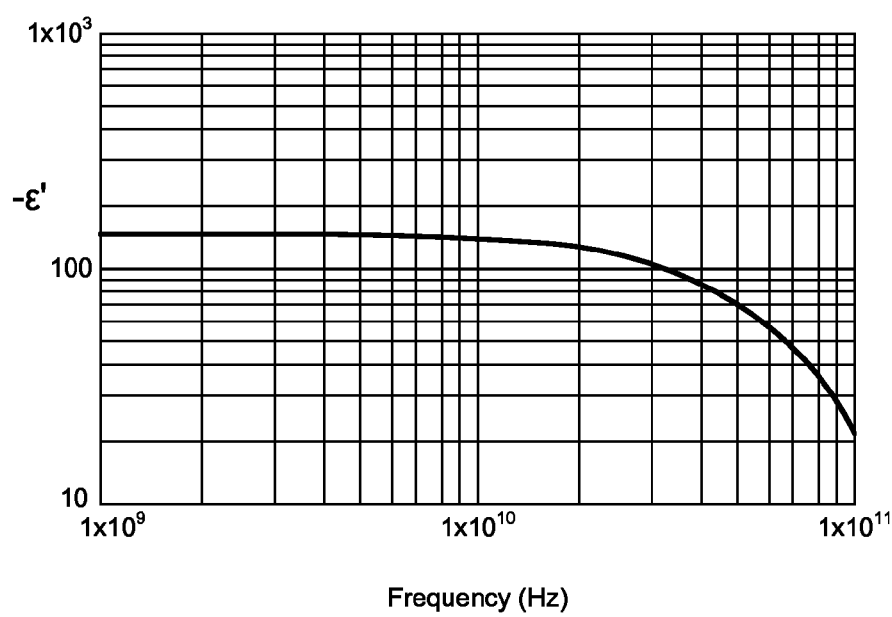
FIG. 3B is a graph illustrating the negative real permittivity of Ge doped to a carrier density of $10^{16}$ per cc as a function of radiation frequency.
Figure 3C:
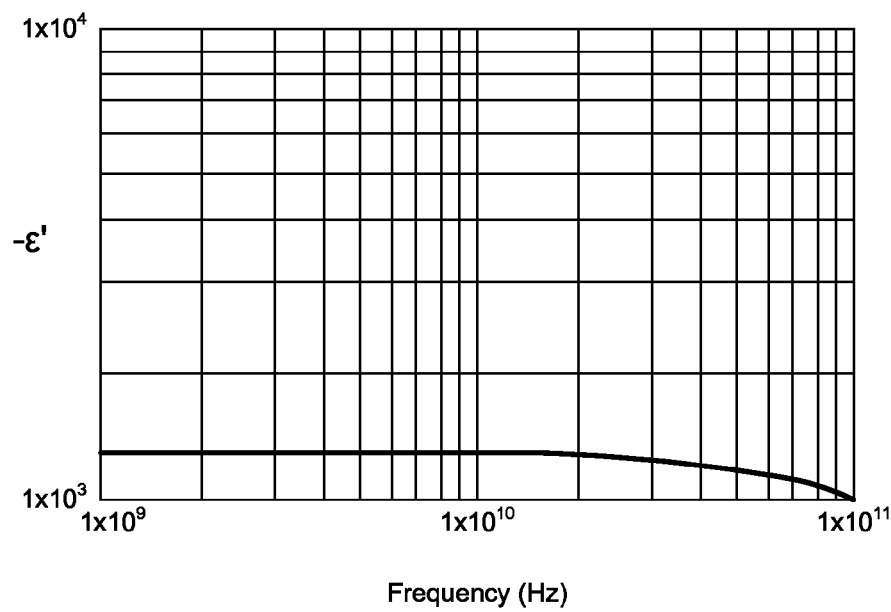
FIG. 3C is a graph illustrating the negative real permittivity of Ge doped to a carrier density of $10^{18}$ per cc as a function of radiation frequency.
Figure 3D:
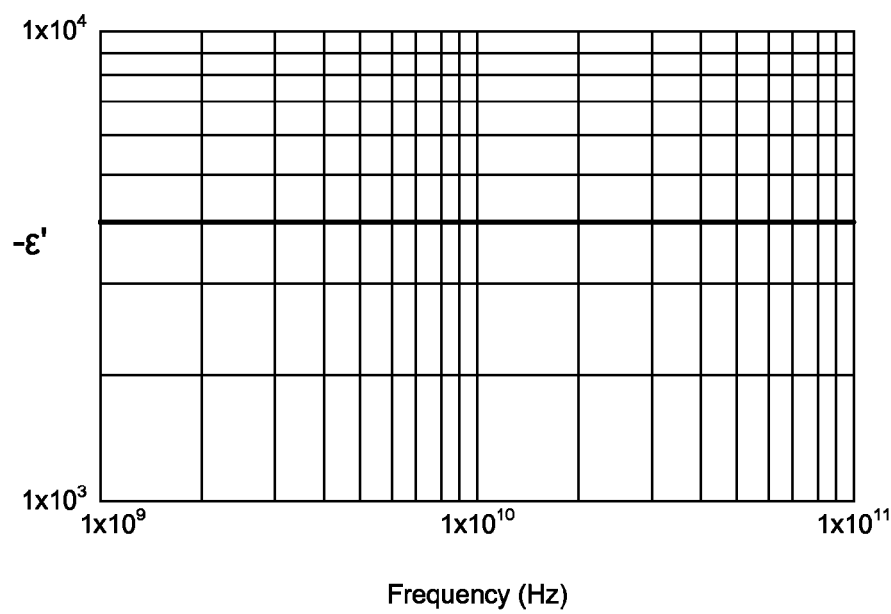
FIG. 3D is a graph illustrating the negative real permittivity of Ge doped to a carrier density of $10^{20}$ per cc as a function of radiation frequency.

The results of the real permittivity calculation for Ge as a function of frequency at various carrier doping densities is shown in FIGS. 3A-3D. FIG. 3A illustrates no doping, that is intrinsic Ge. The real permittivity, $\epsilon'$, over the entire range 1 GHz to 100 GHz is positive, and thus plasmons may not be supported. FIG. 3B illustrates $-\epsilon'$ as a function of frequency for a carrier density of $10^{16}$ per cc. As can be seen in FIG. 3B, $\epsilon'$ is negative up to about 50 GHz, thus supporting plasmons over a portion of the frequency range of 1 to 100 GHz. FIG. 3C illustrates $-\epsilon'$ as a function of frequency for a carrier density of $10^{18}$ per cc. As can be seen in FIG. 3C, $\epsilon'$ is negative over the entire range of 1 GHz to 100 GHz, thus supporting plasmons over the entire range. FIG. 3D illustrates $-\epsilon'$ as a function of frequency for a carrier density of $10^{20}$ per cc. As can be seen in FIG. 3D, $\epsilon'$ is negative over the entire range of 1 GHz to 100 GHz, thus supporting plasmons over the entire range.

Thus, as demonstrated in FIGS. 1A-4C, by choosing an appropriate carrier density in Si, Ge, and GaAs, all of these semiconductor materials may be used as an appropriate plasmonic nano-particle antenna in the RF region of 1 GHz to 100 GHz.

Enhanced Performance of Nano-Particles Based on Size

The performance of the semiconductor nano-antennas may be enhanced by arranging the semiconductor nano-antennas in an array, where the nano-antennas are of an appropriate size, shape, and spacing between nano-antennas. Resonantly coupled plasmonic detectors are described in, for example, U.S. Pat. No. 8,492,727 to Brown, incorporated herein by reference. As a starting point, the plasma responses of single rods (nano-particles), without resonant coupling between rods, of Si, Ge, and GaAs semiconductor materials as a function of rod length, and for three different GHz region frequencies of interest, is shown in FIGS. 4-6.

Figure 4:
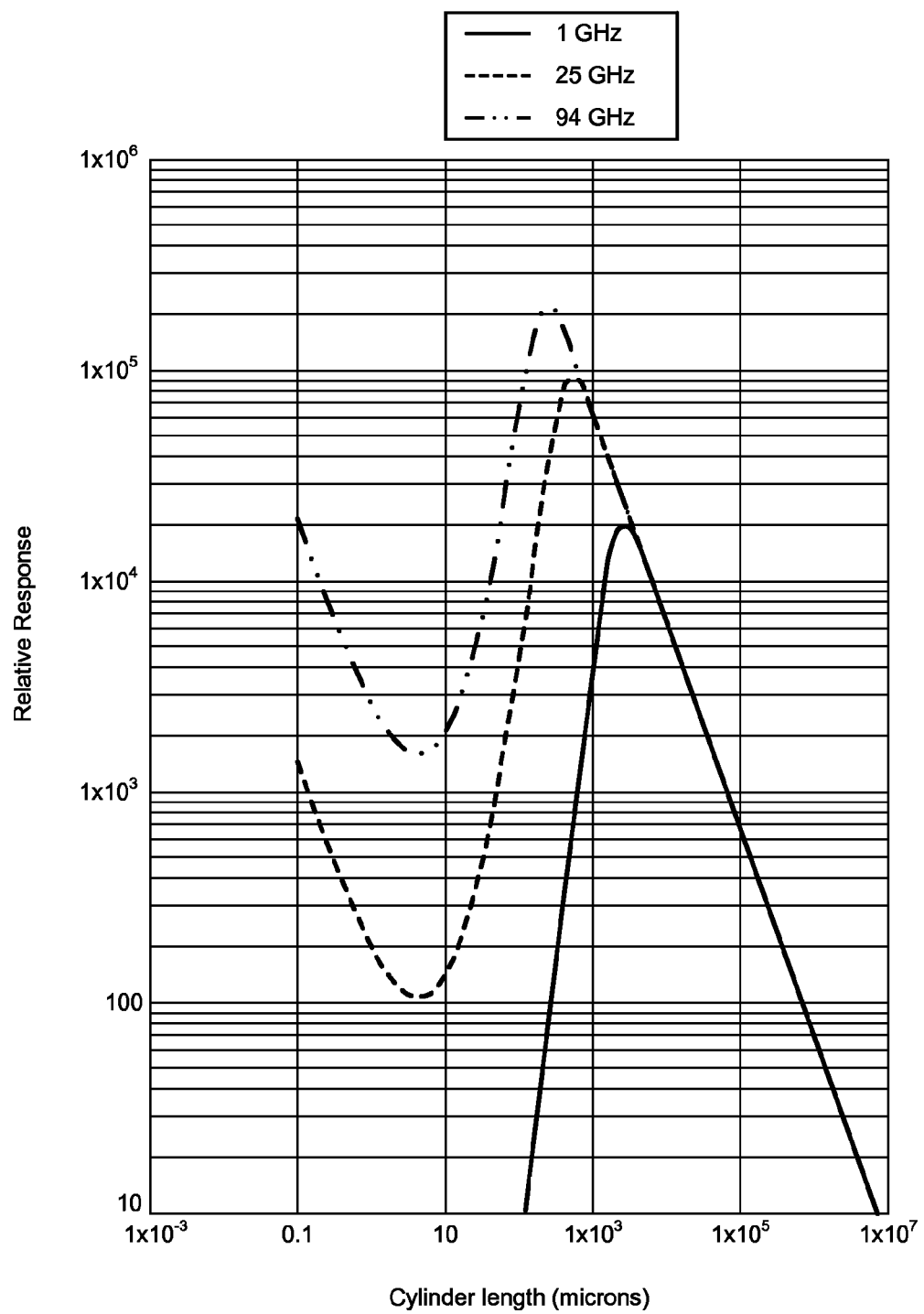
FIG. 4 is a graph illustrating the relative response of radiation at frequencies of 1 GHz, 25 GHz and 94 GHz for a Si rod 10 microns in diameter as a function of rod length.
Figure 5:
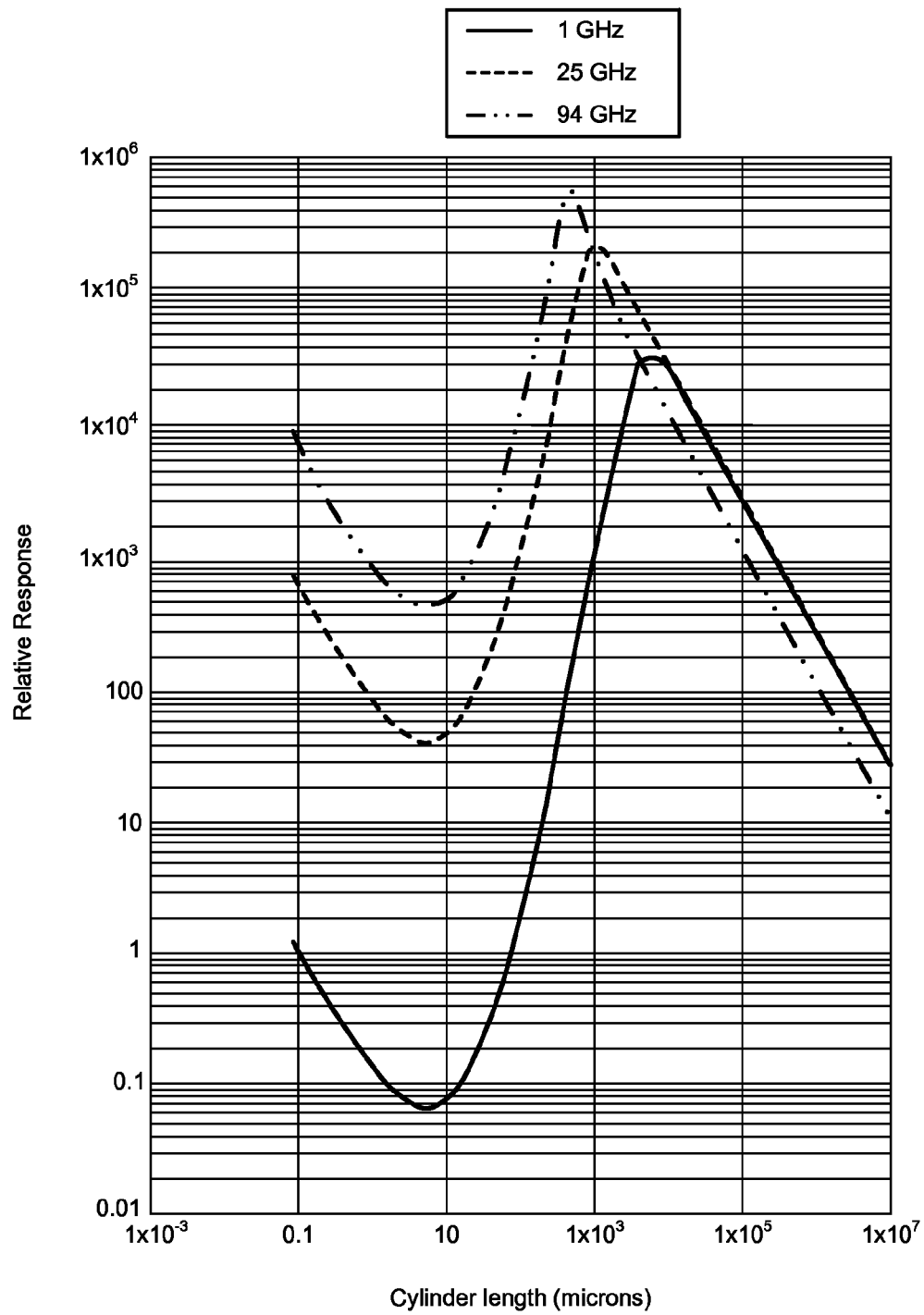
FIG. 5 is a graph illustrating the relative response of radiation at frequencies of 1 GHz, 25 GHz and 94 GHz for a Ge rod 10 microns in diameter as a function of rod length.
Figure 6:
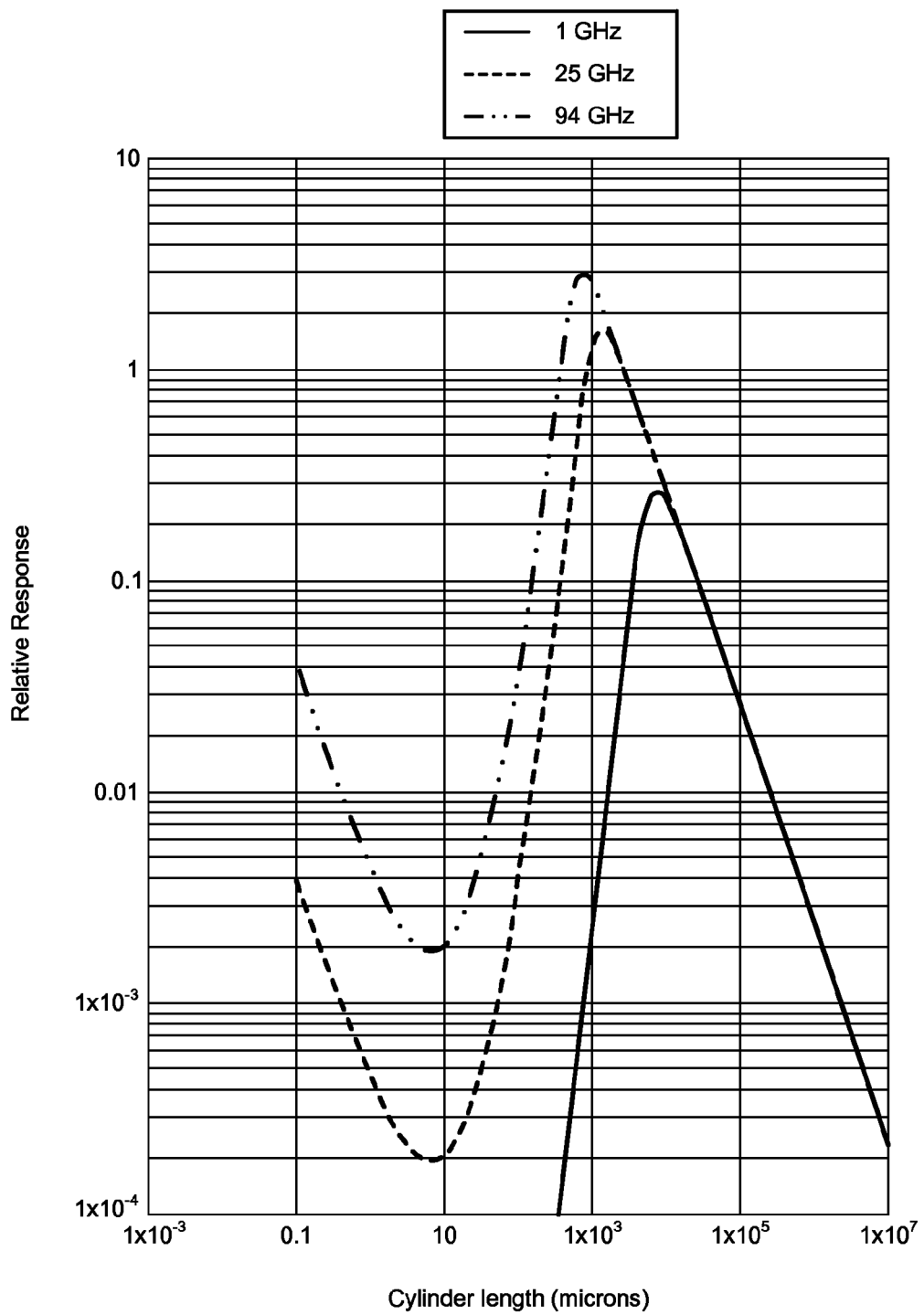
FIG. 6 is a graph illustrating the relative response of radiation at frequencies of 1 GHz, 25 GHz and 94 GHz for a GaAs rod 10 microns in diameter as a function of rod length.

In FIGS. 4-6, the relative response at the three frequencies of 1 GHz, 25 GHz and 94 GHz is shown as a function of cylinder length for micro cylinders of semiconductor material, where the rods (nano-particles) are 10 microns in diameter. For Si semiconductor material shown in FIG. 4, the rod resonance responses for 1 GHz, 25 GHz and 94 GHz frequencies are clustered around a length of about $10^3$ microns (1 mm). In a similar fashion, for Ge semiconductor material shown in FIG. 5, the rod resonance responses for 1 GHz, 25 GHz and 94 GHz frequencies are clustered around a length of about $10^3$ microns. In another similar fashion, for GaAs semiconductor material shown in FIG. 6, the rod resonance responses for 1 GHz, 25 GHz and 94 GHz frequencies are clustered around a length of about $10^3$ microns. Thus, a rod (nano-particle) length of about $10^3$ microns provides the best response for the range of 1 to 94 GHz.

Electric Field Enhancement Based on Gap Between Nano-Particle

Figure 7:
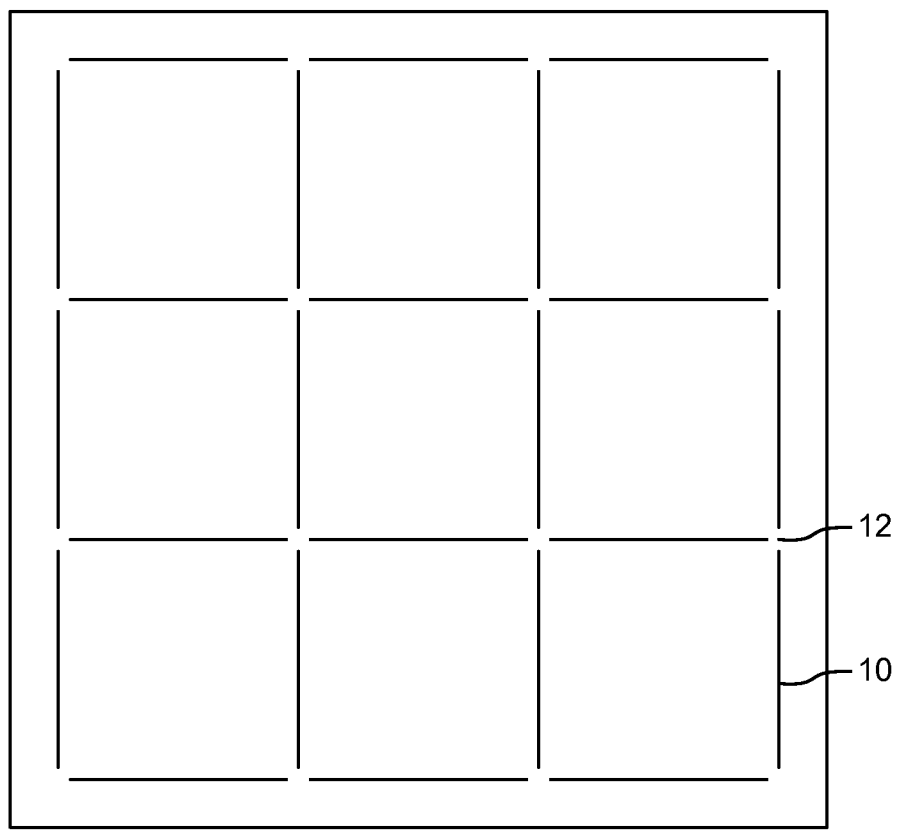
FIG. 7 is a schematic illustrating an array of nano-rods in a checkerboard pattern with gaps between the nano-rods.

FIG. 7 illustrates an array of nano-particles 10, nano-rods, in a checkboard pattern for illustrating an array of nano-antennas. The nano-particles 10 are in a nano-rod shape with a length of 1 mm and 10 microns for the purpose of illustration and calculation. In the checkerboard pattern, the nano-particles 10 are arranged to have symmetric T shapes for each pair of parallel rods and the nearest orthogonal rod where the gap 12 occurs. Gaps 12 are on the order of 10 microns for such a geometry for the purpose of illustration and calculation.

Figure 8A:
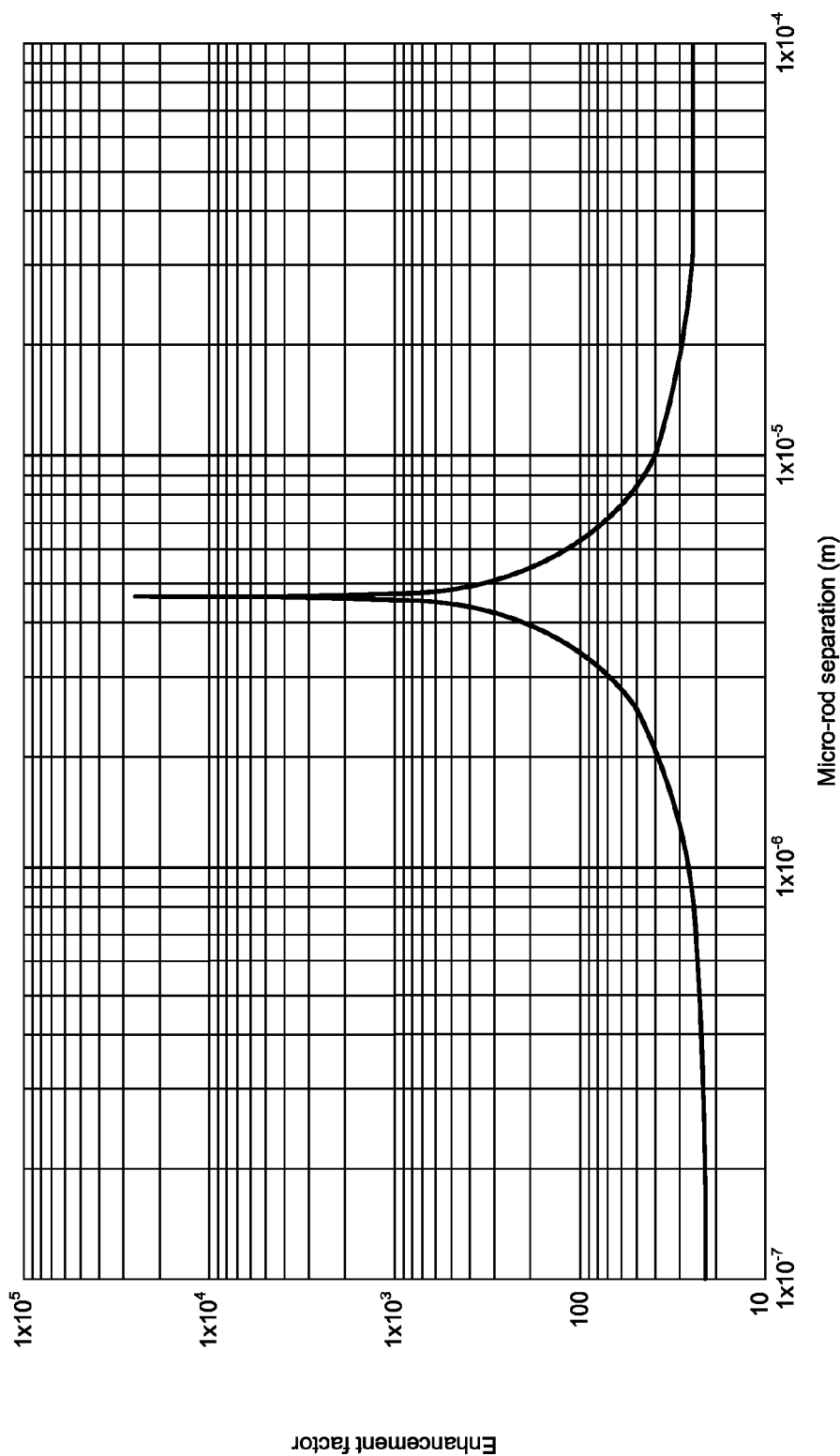
FIG. 8A is a graph illustrating the electric field enhancement of Si nano-rods arranged as in FIG. 7 as a function of the nano-rod separation or gap.
Figure 8B:
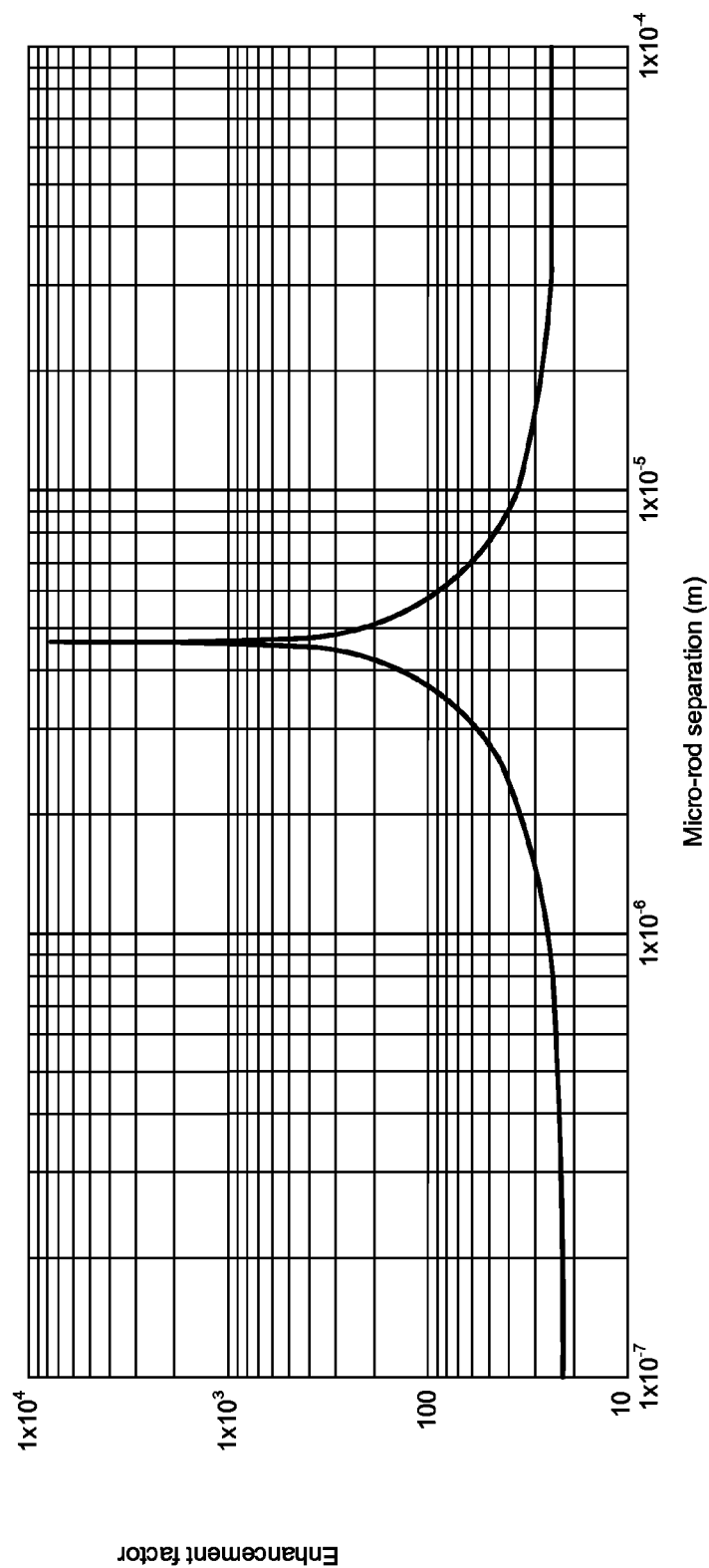
FIG. 8B is a graph illustrating the electric field enhancement of Ge nano-rods arranged as in FIG. 7 as a function of the nano-rod separation or gap.
Figure 8C:
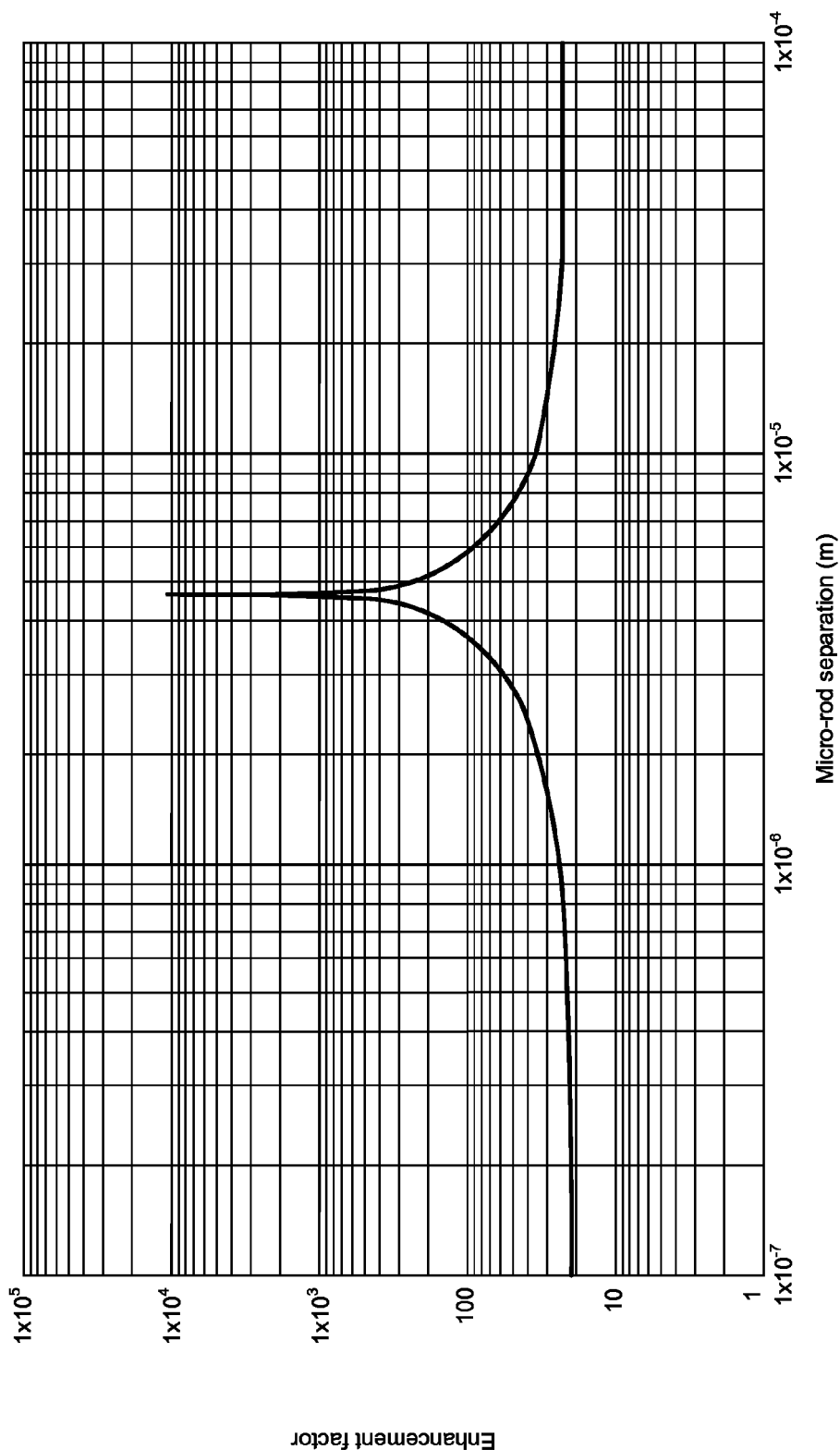
FIG. 8C is a graph illustrating the electric field enhancement of GaAs nano-rods arranged as in FIG. 7 as a function of the nano-rod separation or gap.

FIGS. 8A, 8B and 8C illustrate the electric field enhancement, in the gaps 12 for the arrangement of FIG. 7 for Si, Ge, and GaAs material, respectively. In particular, FIGS. 8A, 8B and 8C illustrate the enhancement factor of the electric field as a function of the nano-particle 10 separation or gap. The enhancement factor is the relative increase of the electric field as compared to the incident electric field. As can be seen, enhancement factors of $10^3$ to $10^4$ are possible with Si, Ge, and GaAs semiconductor materials.

Figure 9A:
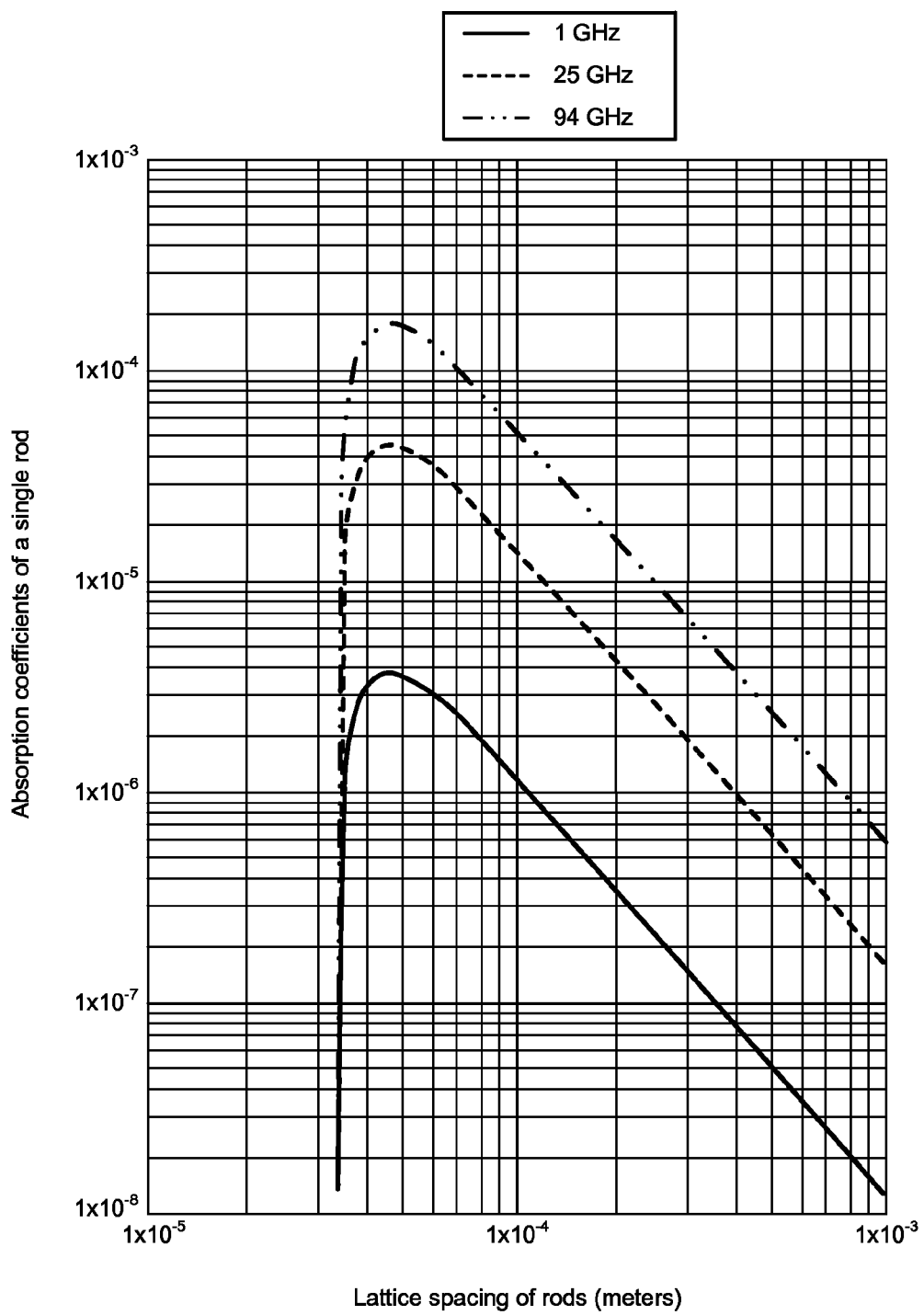
FIG. 9A is a graph illustrating the absorption coefficient of an array of Si nano-rods for radiation frequencies of 1 GHz, 25 GHz and 94 GHz as function of spacing between the nano-rods.
Figure 9B:
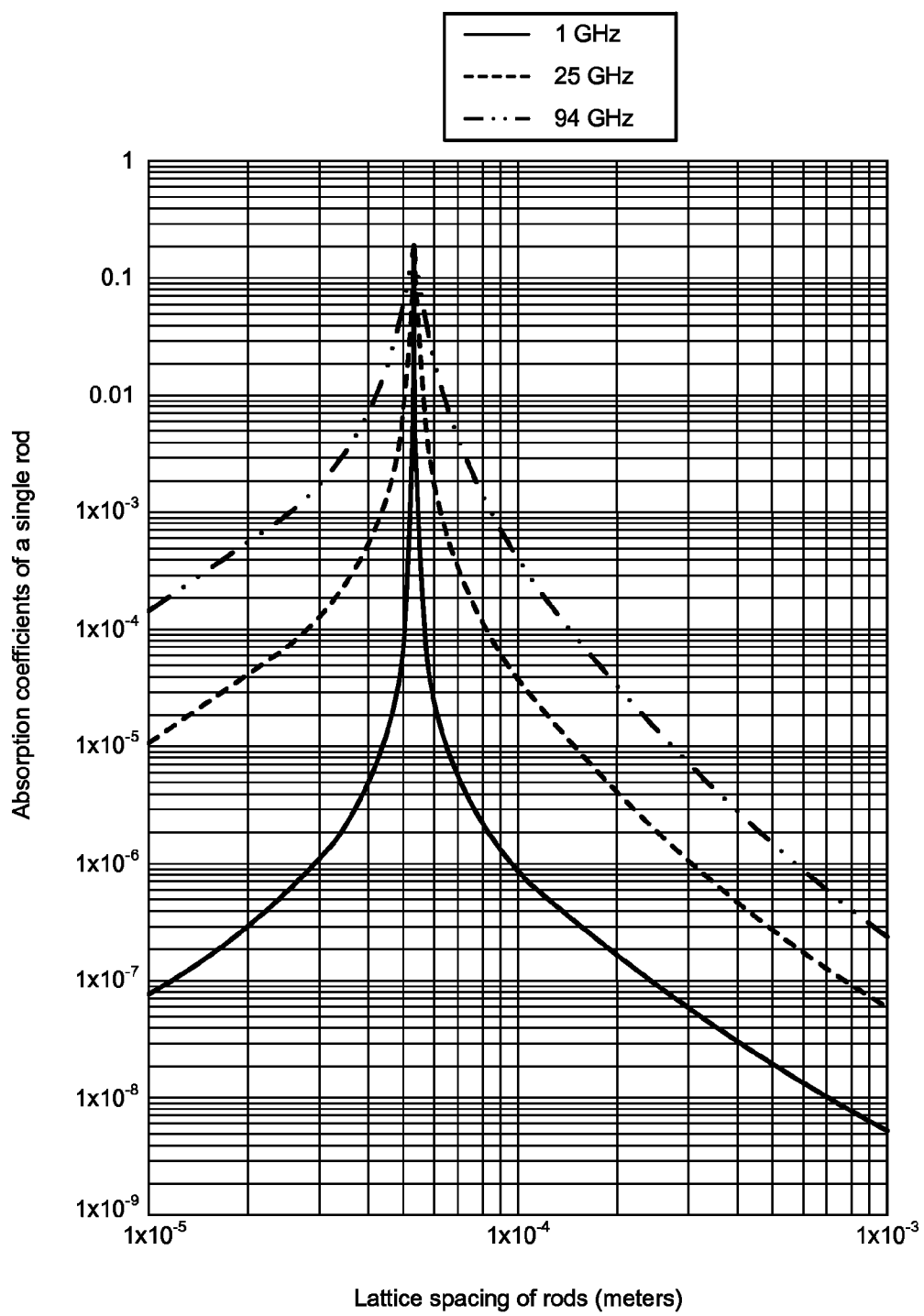
FIG. 9B is a graph illustrating the absorption coefficient of an array of Ge nano-rods for radiation frequencies of 1 GHz, 25 GHz and 94 GHz as function of spacing between the nano-rods.
Figure 9C:
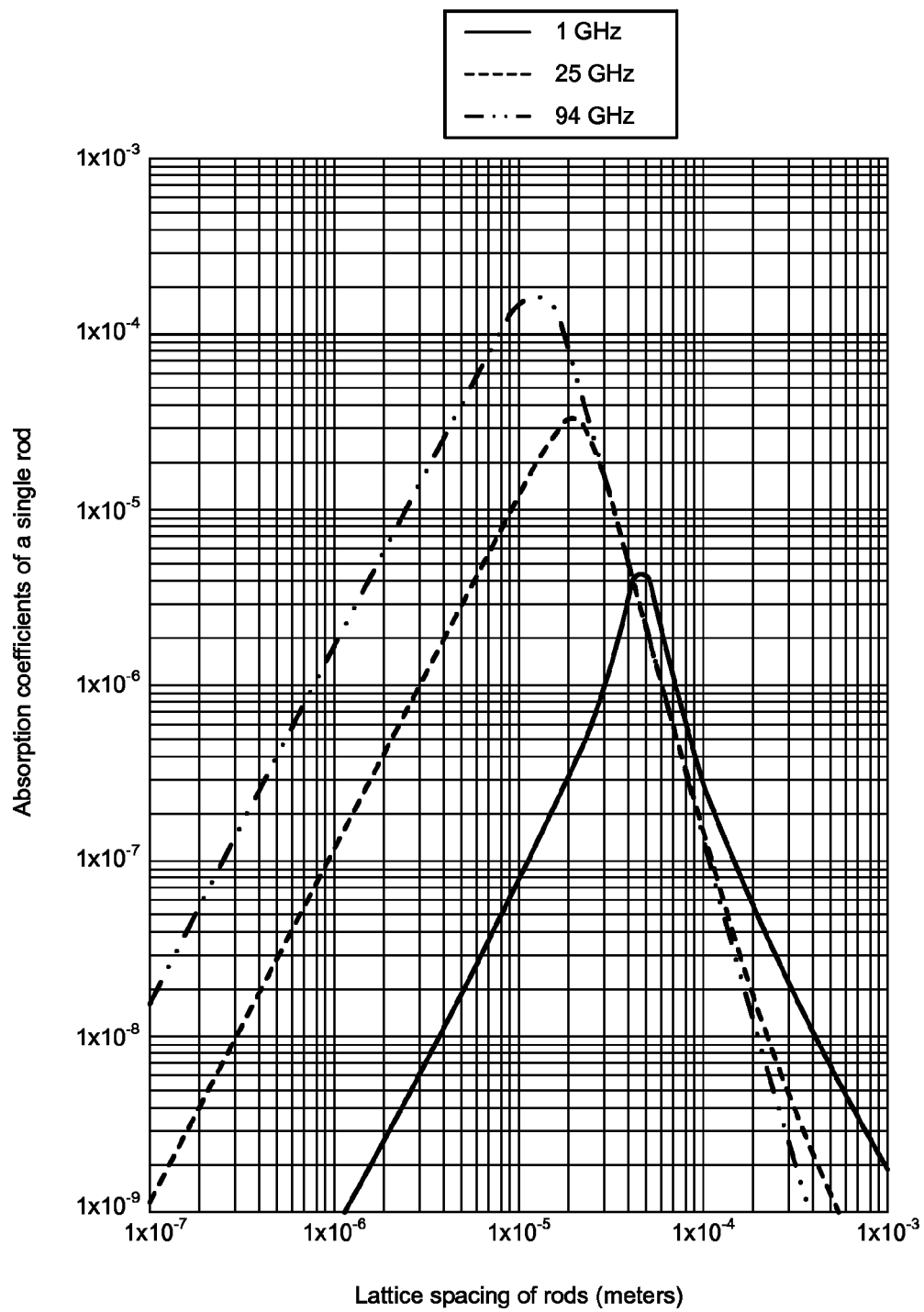
FIG. 9C is a graph illustrating the absorption coefficient of an array of GaAs nano-rods for radiation frequencies of 1 GHz, 25 GHz and 94 GHz as function of spacing between the nano-rods.

FIGS. 9A, 9B and 9C illustrate the absorption coefficient of an array of nano-particle rods arranged as in FIG. 7 for 1 GHz, 25 GHz and 94 GHz frequencies of incident radiation. Each rod is 10 microns in diameter and has a length of $10^3$ microns. FIGS. 9A, 9B and 9C illustrate calculations for semiconductor materials of Si, Ge, and GaAs, respectively.

The absorption response may be enhanced further if antenna elements are arranged not on a square lattice checker board array such as shown in FIG. 7, but instead aligned with the crystallographic directions occurring naturally in the different semiconductors. Thus, the shapes of the nano-antenna elements may be aligned with atomic planes and directions. Si and Ge both have a diamond crystal lattice structure, a face centered cubic structure. GaAs has a zincblende crystal lattice structure. Both semiconductors structures offer a rich variety of crystal planes and directions with which nano-antenna elements may be aligned. The choice of preferred directions is dictated by the value of effective mass of the electrons desired to be used in the nano-antenna design; as well as the desired polarization and radiation lobe antenna responses.

Nano-Antenna Designs for Semiconductor Antenna

The semiconductor antenna with semiconductor nano-antennas may have a variety of arrangements. Designs may be based on metal antenna designs such as simple dipole/gap antennas, log-periodic antennas, and Yagi antennas, for example. Such designs may be used in the implementation of semiconductor nano-antenna arrays, where the use of semiconductor materials provides for parameters such as effective electron mass and crystallography, which permit the control of operating frequencies, size, polarization, and other parameters important in antenna engineering.

Figure 10A:
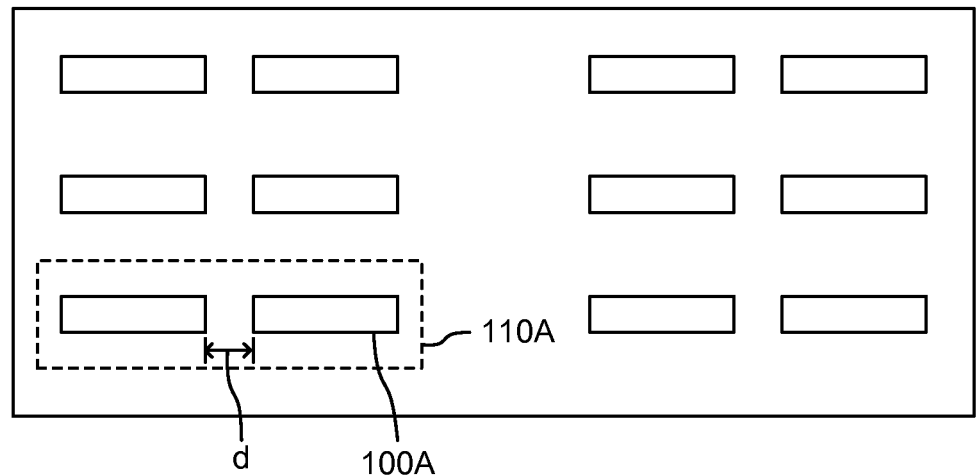
FIG. 10A is a schematic of simple dipole semiconductor nano-antennas according to an embodiment of the invention.

FIG. 10A illustrates a design based on an array of simple dipole semiconductor nano-antennas. Each dipole semiconductor nano-antenna 110A in the array is made up of two nano-particles 100A, with a gap d between the nano-particles 100A. As an example, the nano-particles 100A may have a length of about 1 mm and a diameter of about 10 microns. The gap d may also be about 10 mircons.

Figure 10B:
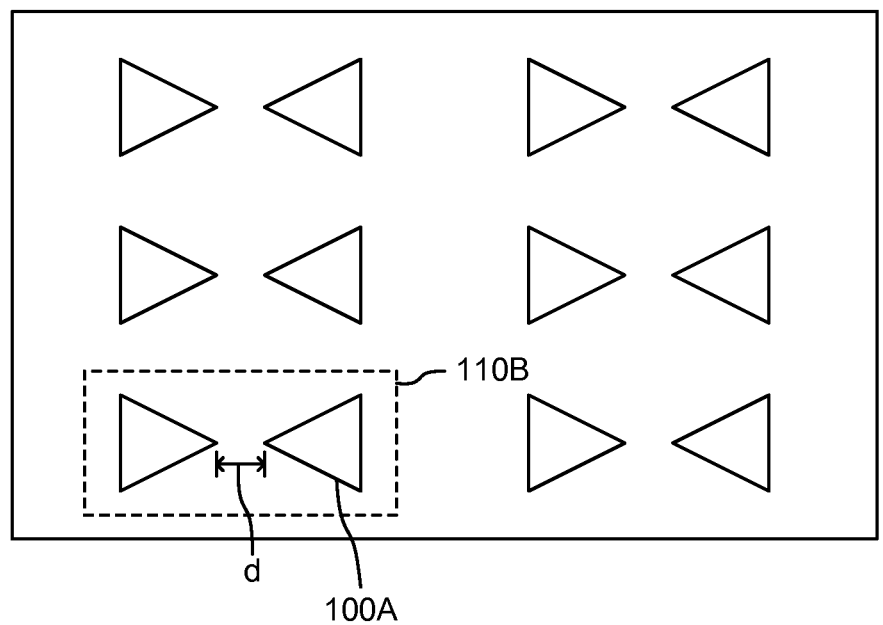
FIG. 10B is a schematic of bow-tie shaped semiconductor nano-antennas according to an embodiment of the invention.

FIG. 10B illustrates a design based on an array of bow-tie shaped semiconductor nano-antennas. Each bow-tie shaped semiconductor nano-antenna 110B in the array is made up of two triangular shaped nano-particles 100B, with a gap d between the nano-particles 100A.

While FIGS. 10A and 10B illustrate an array of semiconductor nano-antennas, alternatively, the semiconductor antenna may comprise a single semiconductor nano-antenna. If in array form, the semiconductor antennas of FIGS. 10 A and 10B may be in the form of phased arrays.

In the array designs of FIGS. 10A and 10B, the gap d may be such that the electric fields surrounding the gaps both extends outside those gaps, and penetrates an intimately adjacent medium. This extension of the electric field allows for the coupling of the field to adjacent electronics.

Semiconductor antenna design may provide advantages over metal antenna design, both in electrical control and allowing for direct connection of the antennas. Considering electrical control of antenna elements, by moving to semiconductors from metals, it is possible for direct electrical control of antenna properties through either applied electric fields across the semiconductor material to divert electrons, or controlled carrier injection to increase (decrease) the effective doping density and thus the effective real permittivity $\epsilon'$ upon which the subtle control of plasmons and thus antenna behavior is fundamentally dependent. Further, semiconductor antennas allow for the direct connection of the antennas to receivers and transmitters because high electric field strengths associated with (and surrounding) the antenna gap can be coupled either electrically (or even non-linear-optically) into adjacent material to control its electrical (or optical) properties.

Integration with MOSFET Circuitry

Figure 11A:
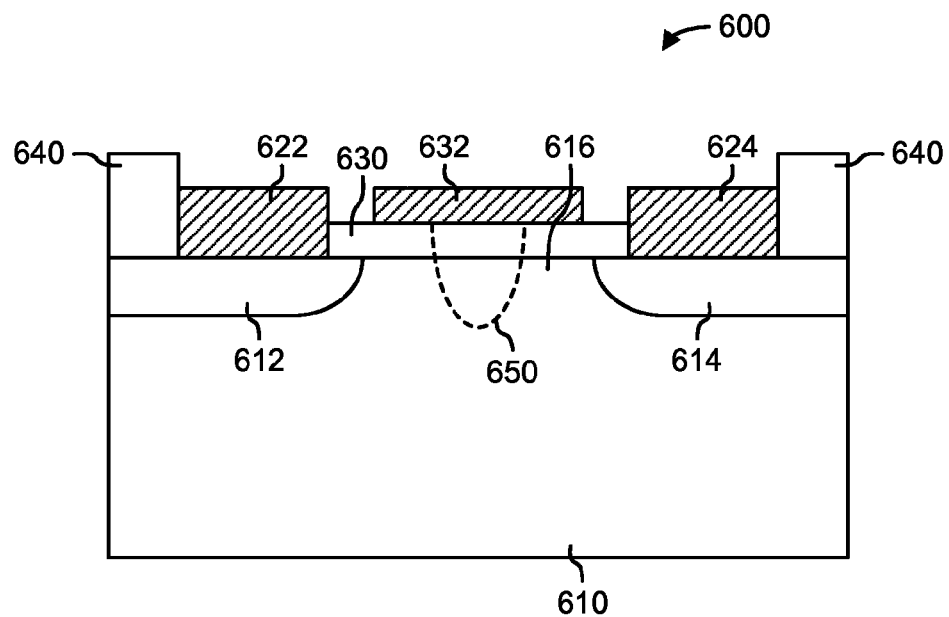
FIG. 11A is cross-sectional view of a MOSFET with a bow-tie shaped semiconductor nano-antenna as a gate according to an embodiment of the invention.
Figure 11B:
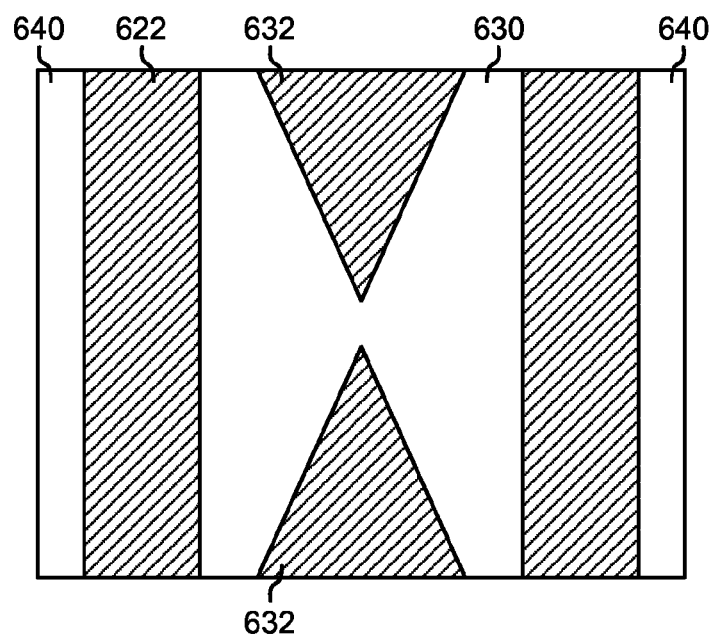
FIG. 11B is top view of the MOSFET of FIG. 11A.

FIGS. 11A and 11B illustrate an electronic device 600, which may be a MOSFET for example, according to an embodiment of the invention. The electronic device 600 has a semiconductor antenna 632 and one or more electronic components coupled to the semiconductor antenna 632, and arranged to receive an electrical signal from the semiconductor antenna 632. The one or more electronic components may monolithically integrated with the semiconductor antenna 632 on a same chip.

The electronic device 600 comprises a semiconductor substrate 610, such as Si. The semiconductor substrate 610 may be p-type, for example. A source region 612 and a drain region 614 are formed in the substrate. The source region 612 and the drain region 614 may be n-wells formed in the semiconductor substrate 610 if the semiconductor substrate 610 is p-type, for example.

A source electrode 622 and a drain electrode 624 are formed to respectively contact the source region 612 and the drain region 614, and are arranged between a gate insulating layer 630 and an insulating layer 640. The source electrode 622 and the drain electrode 624 may be formed of metal, for example.

A semiconductor antenna 632 is formed over the gate insulating layer 630. The semiconductor antenna 632 is formed over the channel region 616 in the semiconductor substrate 610, where the channel region 616 is formed between the source region 612 and the drain region 614.

The semiconductor antenna 632 may have a bow-tie shape, as shown in the FIG. 11B, with a gap between the regions of the bow tie. The semiconductor antenna 632 provides an intensified electric field in the antenna gap. The intensified electric field extends well beyond the gap on either side of the plane of the antenna. FIG. 11A illustrates the extension of the field 650, which can be seen to extend into the channel region 616. Thus, the semiconductor antenna 632 replaces the traditional gate structure for applying a field into the channel region. As with a traditional gate structure, the field due to the semiconductor antenna 632 which extends into the gate region, causes a modulation of the current flow between the source region 612 and the drain region 614. Thus, the high field strength in the gap of the semiconductor antenna penetrates the channel region and directly modulates the current flow between the source region 612 and the drain region 614.

FIGS. 11A and 11B illustrate the dimensions of the semiconductor antenna 632 to be of the same scale as a traditional gate for a MOSFET. For typical MOSFETs which would have a gate of a size on the order of 10 to 100s of nanometers, a semiconductor antenna 632 on the same scale would be appropriate for visible light detection.

Alternatively, for the 1-300 GHz detection range, the antenna sizes would typically be on the order of ~1 mm scale. In this case, a single semiconductor antenna would have a gap size much larger than the remaining components of the MOSFET including the channel region, and multiple channel regions could be addressed by a single semiconductor antenna simultaneously.

The electronic device 600 may be part of an electronic circuit. The electronic circuit may be one of a radio receiver, radio transmitter, radar unit, avionics unit, satellite, chemical sensor, or biological sensor, for example.

The embodiments of the invention have been described in detail with particular reference to preferred embodiments thereof, but it will be understood by those skilled in the art that variations and modifications can be effected within the spirit and scope of the invention.

What is claimed is:

1. A semiconductor antenna comprising:
   a substrate;
   an antenna region comprising semiconductor nano-antenna elements formed on the substrate, wherein the semiconductor nano-antenna elements themselves are formed of a semiconductor material having a doping concentration such that the real part of the permittivity of the semiconductor material is negative over at least a portion of radio frequencies from 1 MHz to 300 GHz, wherein the semiconductor nano-antenna elements are arranged in an array of resonantly coupled plasmonic nano-antennas, the semiconductor nano-antenna elements doped to have a single conductivity type, each semiconductor nano-antenna element comprising two nano-particles separated by a gap.

2. The semiconductor antenna of claim 1, wherein the semiconductor material is one of a single, binary, ternary or quartenary semiconductor compound.

3. The semiconductor antenna of claim 2, wherein the semiconductor material is selected from the group consisting of silicon, germanium, and gallium arsenide.

4. The semiconductor antenna of claim 1, wherein the semiconductor nano-antenna elements are in the shape of dipole gap, Yagi, or log-periodic antennas.

5. The semiconductor antenna of claim 1, wherein the characteristic dimensions of semiconductor nano-antenna elements are in the range of nanometers to millimeters in spatial scale.

6. The semiconductor antenna of claim 1, wherein the semiconductor nano-antenna elements are arranged in a square or rectangular array.

7. The semiconductor antenna of claim 1, wherein the semiconductor nano-antenna elements are aligned with crystal plane or atom vector directions of the semiconductor material.

8. An electronic device, comprising:
   the semiconductor antenna of claim 1; and
   one or more electronic components coupled to the semiconductor antenna, and arranged to receive an electrical signal from the semiconductor antenna.

9. The device of claim 8, wherein the one or more electronic components comprise components of a MOSFET.

10. The device of claim 9, wherein the one or more electronic components are monolithically integrated with the semiconductor antenna on the same chip.

11. The device of claim 9 wherein the gap of the semiconductor antenna is aligned with a gate region of the MOSFET.

12. The device of claim 8, wherein the one or more electronic components are monolithically integrated with the semiconductor antenna on the same chip.

13. An electronic circuit comprising the electronic device of claim 1.

14. The electronic circuit of claim 13, wherein the electronic circuit is one of a radio receiver, radio transmitter, radar unit, avionics unit, satellite, chemical sensor, or biological sensor.

* * * * *